United States Patent [19]
Chan et al.

[11] Patent Number: 5,120,662
[45] Date of Patent: Jun. 9, 1992

[54] MULTILAYER SOLID PHASE IMMUNOASSAY SUPPORT AND METHOD OF USE

[75] Inventors: Emerson W. Chan, Libertyville; Werner Schulze, Waukegan; William G. Robey, Libertyville; Brian P. Braun, Gurnee; Cynthia K. Daluga, Lindenhurst; Andreas A. Kapsalis, Evanston; Kevin M. Knigge, Gurnee; John E. Stephens, Chicago; Joseph J. Stojak, II, Waukegan; David S. Vallari, Grayslake; Benton A. Durley, deceased, late of Antioch, by Roberta W. Durley, executrix; James D. Defreese, Wildwood; Carl W. Merkh, Lindenhurst, all of Ill.

[73] Assignee: Abbott Laboratories, Abbott Park, Ill.

[21] Appl. No.: 532,489

[22] Filed: Jun. 4, 1990

Related U.S. Application Data

[63] Continuation-in-part of Ser. No. 350,180, May 9, 1989, abandoned.

[51] Int. Cl.[5] .................. G01N 33/544; G01N 33/53; G01N 33/566; C12Q 1/00
[52] U.S. Cl. .................... 436/530; 435/7.91; 435/7.92; 435/7.93; 435/7.94; 435/7.95; 435/291; 436/501; 436/809; 436/808
[58] Field of Search ............ 435/4, 7, 7.92, 7.91, 435/970, 7.93, 7.94, 7.95, 291; 436/524, 518, 531, 811, 820, 824, 530, 501, 809, 808

[56] References Cited

U.S. PATENT DOCUMENTS

| | | | |
|---|---|---|---|
| 4,225,485 | 9/1980 | Buckler et al. | 435/7 |
| 4,960,961 | 10/1990 | Gordon et al. | 435/970 |

FOREIGN PATENT DOCUMENTS 0063810  4/1982  European Pat. Off. ............. 435/7

OTHER PUBLICATIONS

Fisher (1988) Catalogue, p. 712.
Thomas Scientific (1988/1989) Catalogue pp. 1094, 1097, 1098.
Johnston et al. 1987. Immunochemistry in Practice, 2nd Ed. Blackwell Sci Pub. London, p. 261.

Primary Examiner—Christine Nucker
Assistant Examiner—David R. Preston
Attorney, Agent, or Firm—Priscilla E. Porembski; Frank S. Ungemach

[57] ABSTRACT

An immunoassay which is capable of simultaneously detecting any desired number of antigens of one infectious agent, or combinations of antigens of several infectious agents, or any desired number of immunoglobulins of one infectious agent, or combinations of immunoglobulins of several infectious agents on a single solid support. A test sample is contacted with a solid support on which one or more antigens are immobilized as discrete test sites. Antigen-antibody complexes are formed and detected on the solid support.

20 Claims, 7 Drawing Sheets

MULTILAYER SOLID PHASE IMMUNOASSAY SUPPORT AND METHOD OF USE

RELATED APPLICATIONS

This is a continuation-in-part application of U.S. Ser. No. 350,180 filed May 9, 1989, entitled "PROCESS FOR PREPARING AN IMPROVED WESTERN BLOT IMMUNOASSAY", now abandoned, which enjoys common ownership and is incorporated herein by reference. This application also is a related application to U.S. Ser. No. 227,408 entitled "BIOLOGICAL SAMPLE ANALYZER", filed Aug. 2, 1988, U.S. Ser. No. 227,272 entitled "TEST CARD FOR PERFORMING ASSAYS", filed Aug. 2, 1988, and U.S. Ser. No. 227,590 entitled "REACTION CARTRIDGE AND CAROUSEL FOR BIOLOGICAL SAMPLE ANALYZER", filed Aug. 2, 1988, all of which enjoy common ownership and are incorporated herein by reference.

BACKGROUND OF THE INVENTION

This invention relates generally to immunoassays, and more particularly, relates to a semi-automated assay system to detect and confirm the presence of antibodies, which assay system is an improvement over currently available assays for detection and confirmation of the presence of antibodies.

The human immune system responds to infections by generating antibodies to various antigens. The number of antibodies and the amount of each different antibody produced depends on the infectious agent and the particular antigen(s) which initiate the antibody response.

Current commercially available screening tests available for determining infections are based on enzyme immunoassays (EIAs) to detect the presence of antibodies. Generally, such tests utilize a solid support such as a polystyrene bead or microtiter well coated with a partially purified lysate containing antigens of the infectious agent. A test sample is contacted with the coated solid support, and any antibody which is present in the test sample and specific to the antigen is captured on the solid support, thus forming an antigen-antibody complex. This antigen-antibody complex is contacted with a second antibody labelled with a signal-generating detectable conjugate to form an antigen-antibody-antiantibody complex. The presence and the amount of antibody in the test sample is determined by detecting the signal produced by the conjugate complex. However, the partially purified lysates may contain impurities and disproportionate quantities of various antigens or may lack important antigenic polypeptides. These deficiencies detrimentally affect both the sensitivity and specificity of the assay. Furthermore, it is often difficult to prepare sufficient quantities of partially purified lysates for traditional confirmatory tests, and the lack of a desired antigen increases purification problems.

These screening tests also have known non-specific reactivities. See, for example, J. E. Menetove et al., Lancet: 1213 (Nov. 21, 1987); D. Barnes, Science 238: 884-885 (1987); A. Puckett et al., Lancet: 714 (Mar. 26, 1988). A majority of the non-specificity is attributable to immunoreactivities with normal human antigens that are present in these lysates of the infectious agent. The normal human antigens (cellular protein impurities) originate from the tissue culture cells or other culture media that are used to propagate the infectious agent, and they are the major constituents of partially purified lysates.

The major surface antigen of Human Immunodeficiency Virus (HIV), gp120, and the HIV transmembrane antigen gp41 are readily lost during viral purification. H. Gelderblood et al., *Virology* 156: 171-176 (1987). These HIV envelope antigens thus often are underrepresented in viral lysates.

Consequently, a confirmatory test is required to corroborate reactive results obtained with the currently available licensed screening tests for HIV. The protocol for performing such confirmatory tests typically involves repeating the screening test to ensure a reactive test sample, and then performing a Western blot (WB) test on these repeat reactive test samples to confirm the reactive screening result. Those test samples which also are reactive by the WB test are considered as confirmed positive for HIV exposure.

The typical Western blot test is described by Gordon et al., U.S. Pat. No. 4,452,901. This test initially involves separating the antigens of a viral lysate according to size by SDS-PAGE under reducing conditions. The invisible bands of antigens in the gel then are electrophoretically transferred (transblotted) intact onto a sheet of nitrocelluose. This sheet then is cut into strips perpendicular to the bands. The strips are allowed to react with individual test samples and the reactive antibodies are detected by EIAs analogous to the screening assay. The resultant color reaction yields a pattern of stained bands revealing those antigens for which the test sample is seropositive. The WB test therefore has an advantage over screening tests because the antigens in the viral lysate which are reactive with the individual antibodies can be visualized separately. Additionally, non-viral reactivities in the inter-band areas can be identified and disregarded.

Despite the recited advantages of the Western blot test over traditional screening assays, the WB test has its drawbacks. See, for example, G. Biberfeld et al., *Lancet* ii: 289-290 (1986); C. L. Van de Poel et al., *Lancet* ii: 752-754 (1986); and A. M. Courouce, *Lancet* ii: 921-922 (1986). Traditional immunoblot methods such as the WB test lack reproducibility because viral lysates may vary in antigenic concentration.

The WB test reportedly lacks sensitivity, particularly in regard to the HIV envelope (ENV) antigens. A. Saah et al., *J. Clin. Micro.* 259: 1605-1610 (1987). We have observed that this is partly due to the preferential loss of the major surface antigen gp120 during virus maturation and purification, and partly due to the fact that gp120 is reduction sensitive. Its antigenicity is especially reduced in WB tests that utilize reducing SDS-PAGE. Further, the serologically most important HIV transmembrane ENV antigen gp41 (M. G. Sarngadharan et al., *Ann. Inst. Pasteur/Virol.* 138: 133-136 [1987]) characteristically gives a diffuse band on Western blots due to variable glycosylation; this band is quite weak when compared to the band produced by the p24 antigen. Moreover, the gp41 reactive band is especially weak when compared with the blots which utilize recombinant p41 antigen.

The Western blot test also yields a number of non-specific reactivities. The non-specific reactivities yield bands that sometimes overlap the true antigen bands. For example, we have observed that p24-only, p17-only, atypical gp41, or p70-only reactivities are those most likely to be false reactivities.

Further, the WB test yields extra bands of reactivities that are partly due to partially cleaved or uncleaved viral precursor proteins which may appear between the main antigenic bands. These extra reactivities also may be due to aggregations or degradations of viral antigens. For example, an HIV gp120 band may be due to a trimeric aggregation of gp 41. S. Zolla-Pazner et al., *New England J. Med.* 320: 18–19 (1989). Both HIV gp41 and p24 are known to yield dimers, trimers, and tetramers despite reducing conditions during electrophoresis. Using monoclonal antibodies, we have observed that HIV gp120 can give rise to two other bands, gp80 and gp45. These two bands represent the N-terminal ⅔ and C-terminal ⅓ of gp120, respectively. They are most likely degradation products in viral lysates resulting from a specific cleavage of the gp 120.

Further problems with the WB test include minor bands of reactivity due to the presence of regulatory proteins such as nef, VPR, VPV, etc; the amount of time required for the test which usually involves an overnight incubation step; the manual nature of the test; the subjectiveness of the test results due to the visual readout; and the ability to detect only one strain of a particular virus per sample tested. Thus, the WB confirmatory test exhibits poor sensitivity, particularly in regard to the important HIV ENV markers, with an abundance of additional non-specific and specific bands and technical problems which make band identification difficult and turn-around time long.

The problems associated with using lysates of infectious agents in the WB test partially can be avoided by expressing desired antigenic polypeptides in various heterologous cell systems. These systems use recombinant techniques to insert the infectious agent genes of interest in cells that can produce quantities of these polypeptide products. This procedure often results in the production of the desired antigen in sufficient quantities, but typically is associated with the presence of new impurities and degraded antigenic fragments. Antigens produced by these methods also may form aggregates that must be minimized by using reducing agents or require the use of multiple gels to avoid both aggregation and degradation problems.

The use of several antigens in a single assay has been described. Lin et al., *J. Virol.* 59: 522–524 (1986) describes a dual antibody probing technique that permitted identification of Epstein-Barr virus and different herpes virus antigens in the same Western Blot test.

It also is possible to use multiple detection methods on a single Western blot test. Lee et al., *J. Immuno. Methods* 106: 27–30 (1988) describes a technique which uses sequentially applied sets of probing antibodies, enzyme-conjugated developing antibodies and enzyme substrates to detect two or more types of interferon on a single Western blot test. The same result can be achieved by simultaneously applying more than one type of probing antibody using a mixture of different enzyme-conjugated developing antibodies followed by successive applications of different substrates.

Gordon et al., European Patent Application Publication No. 0 063 810, published Mar. 11, 1982, describe immunoassay devices and kits comprising antigens or antibodies or both bound to a solid support. The use of the described solid supports makes possible a number of simultaneous antibody-antigen reactions in one operation. Gordon et al. describe applying single or successive doses of solutions of antigens or antibodies to the surface of the solid support using a pipet or syringe. In a preferred embodiment, the antigen is applied as a microdot formed by adding small volumes of an antigenic solution. The application however does not describe immunoassays using antigens purified from a complex mixture of proteins.

Lefkovits, WO 87/03965, published Jul. 2, 1987, describes a test strip for several simultaneous assays. The test strip is made from nitrocellulose impregnated with an antibody that is cut into strips and mounted on an inert backing. The soaking of a support sheet in a solution of antigenic peptide and then cutting the sheet into strips also is described, but the transferring of the antigen to the solid support electrophoretically is not taught in the publication.

It would be advantageous to provide an assay system which could be used as a confirmatory test in place of the Western blot or Western blot-based tests. Such an assay system would utilize highly purified monomeric antigens of infectious agents which are essentially free from impurities, aggregates or degraded fragments. This assay system therefore would have improved specificity compared with currently available screening and confirmatory tests. It also would be advantageous to provide an assay system which is semi-automatable with a non-subjective readout and therefore easier to evaluate than the WB test. Another advantage of such an assay system is the ability to use it as a research tool to better understand patterns of serological markers associated with viral infection, particularly in the case of Hepatitis C Virus, for which the virus has not been isolated. It additionally would be advantageous to provide a test which could differentiate HIV-1 and HIV-2 from each other by providing side-by-side comparative data, thus a test that is capable of detecting both HIV-1 and HIV-2 and also capable of distinguishing one type from the other. It further would be advantageous to provide an assay system which would allow for the simultaneous detection of a panel of multiple antigens or antibodies.

SUMMARY OF THE INVENTION

This invention provides an immunoassay to simultaneously detect the presence or amount of at least one antibody which may be present in a test sample, which method comprises contacting a test sample with a solid support on which one or more antigens are immobilized as discrete test sites, for a time and under conditions sufficient to form antigen-antibody complexes, and detecting the presence of said complexes present on said solid support. The solid support may be nitrocellulose, and the discrete test sites may be immunodot blots. The solid support may be contacted with a blocking agent prior to contacting the solid support with the test sample. The antigen-antibody complexes are detected by contacting the complexes with a conjugated signal generating system which is capable of yielding a quantitatively measurable signal correlated to the signal of normal test samples to indicate antibody positive or antibody negative for the test sample. Antibodies which can be detected by the invention include Human Immunodeficiency Virus (HIV)-1, HIV-2 and Hepatitis C Virus (HCV).

This invention also provides an immunoassay to detect the presence or amount of at least one antigen which may be present in a test sample, which method comprises contacting a test sample with a solid support on which one or more antibodies are immobilized as discrete test sites, for a time and under conditions sufficient to form antigen-antibody complexes, and detecting the presence of said complexes present on the solid support. The solid support may be nitrocellulose, and the discrete test sites may be immunodot blots. The solid support may be contacted with a blocking agent prior to contacting the solid support with the test sample. The antigen-antibody complexes are detected by contacting the complexes with a conjugated signal generating system which is capable of yielding a quantitatively measurable signal correlated to the signal of normal test samples to indicate antigen positive or antigen negative for the test sample. Antigens which can be detected by the invention include those of Human Immunodeficiency Virus (HIV)-1, HIV-2 and Hepatitis C Virus (HCV).

DETAILED DESCRIPTION OF THE INVENTION

Figure 1:
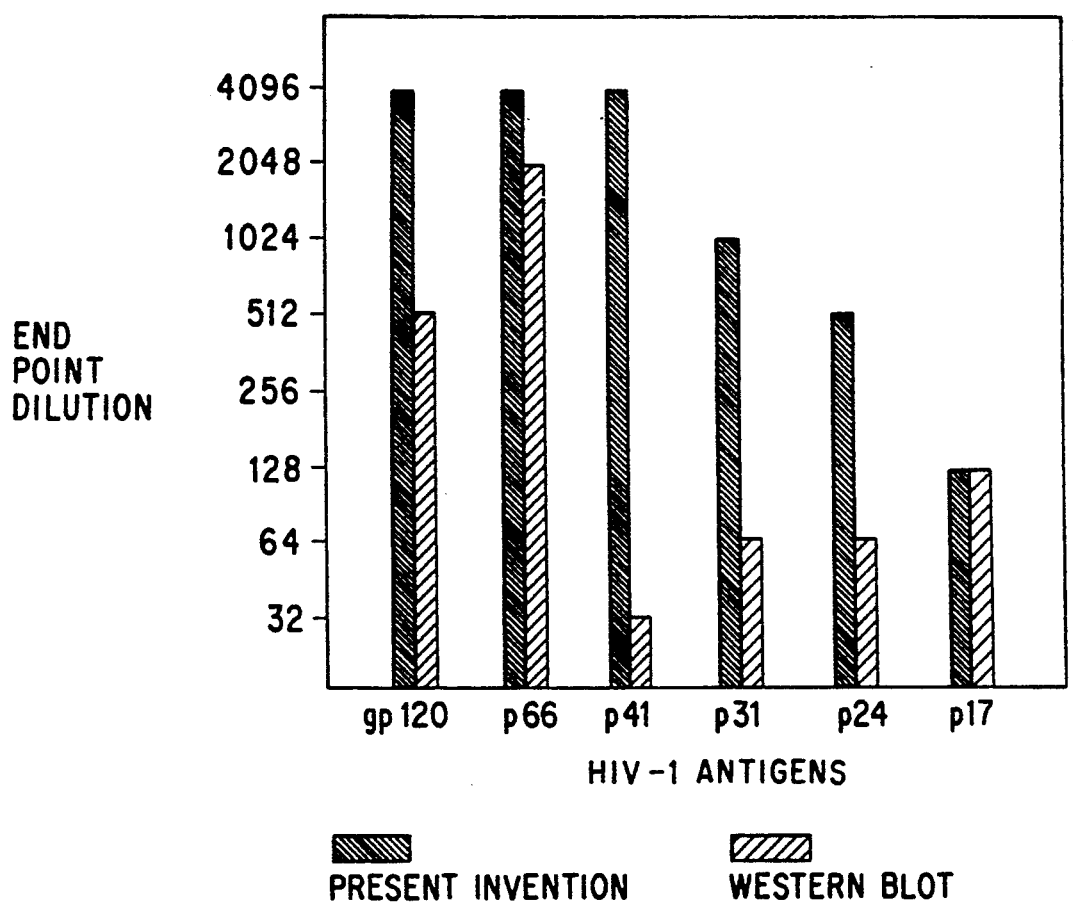
FIG. 1 is a bar graph of an HIV-1 antibody positive serum serially diluted in normal human serum and titered in both the assay system of the invention and a conventional Western blot test.
Figure 2:
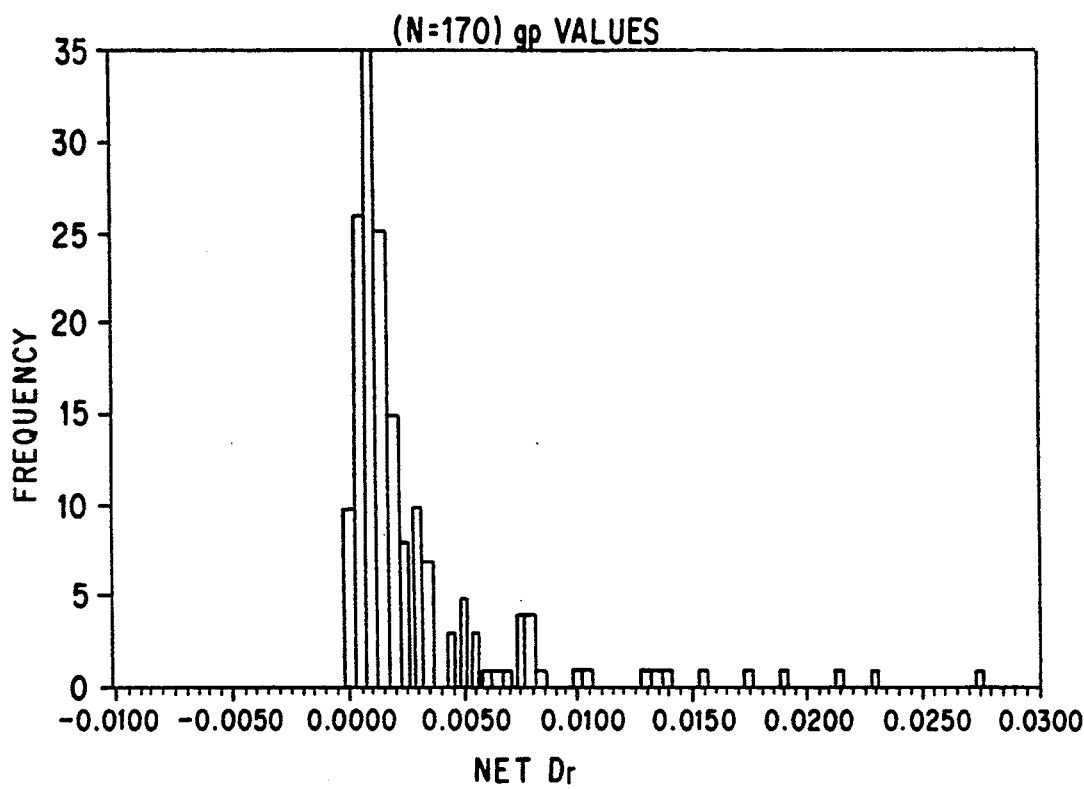
FIGS. 2 to 9 are random donor distribution graphs (N=170) wherein frequency is plotted against net reflectance density (Dr) for the HIV-1 antigens gp 120 (FIG. 2), p66 (FIG. 3), p41 (FIG. 4), p31 (FIG. 5), p24 (FIG. 6), p17 (FIG. 7), HIV-2 p41 antigen (FIG. 8) and procedural (anti-human) values (FIG. 9).
Figure 3:
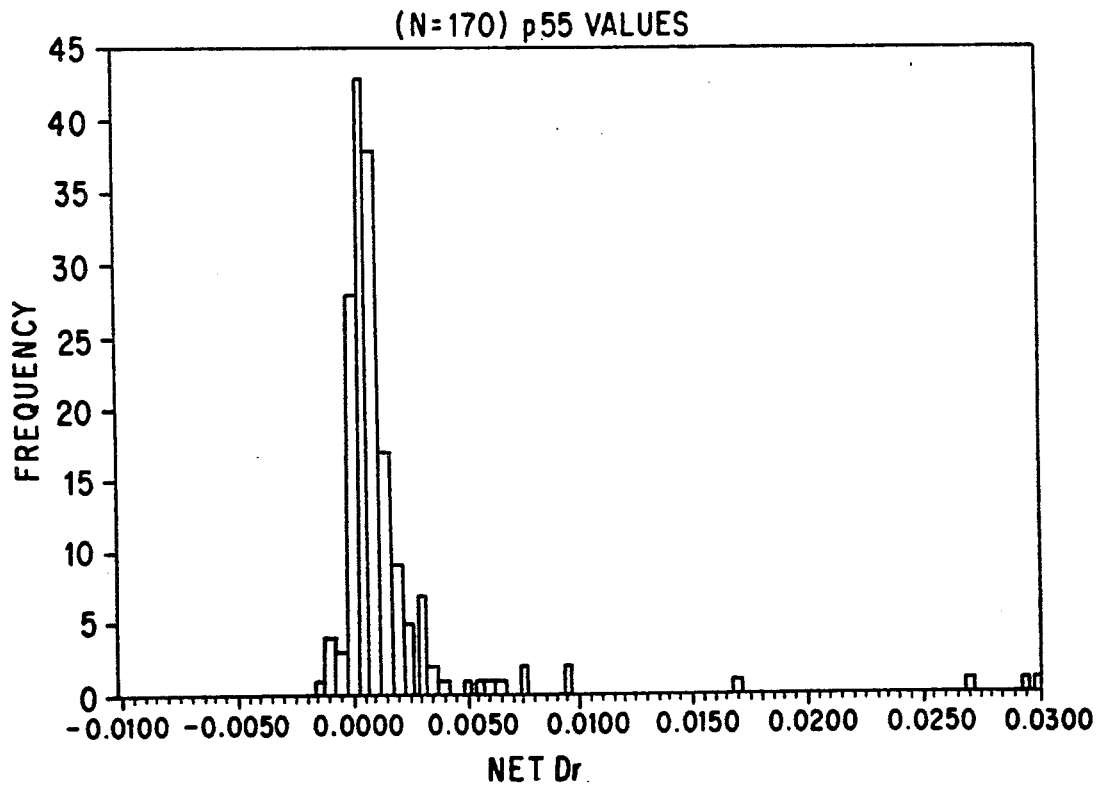
Figure 4:
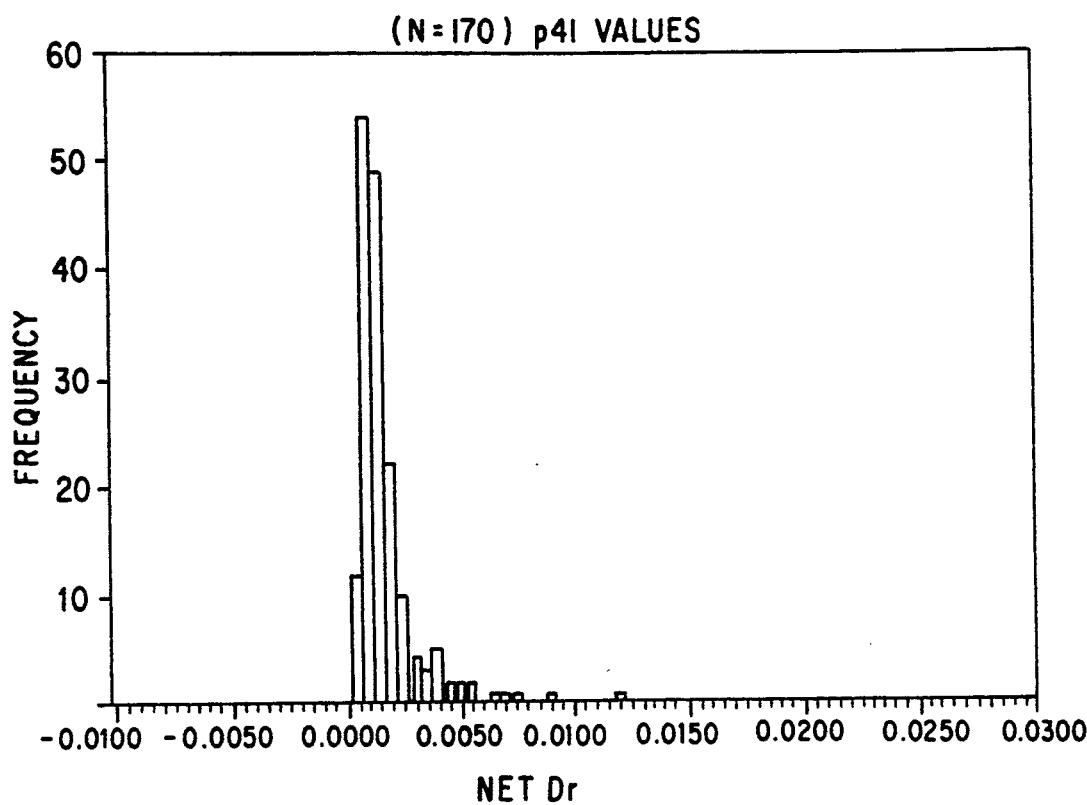
Figure 5:
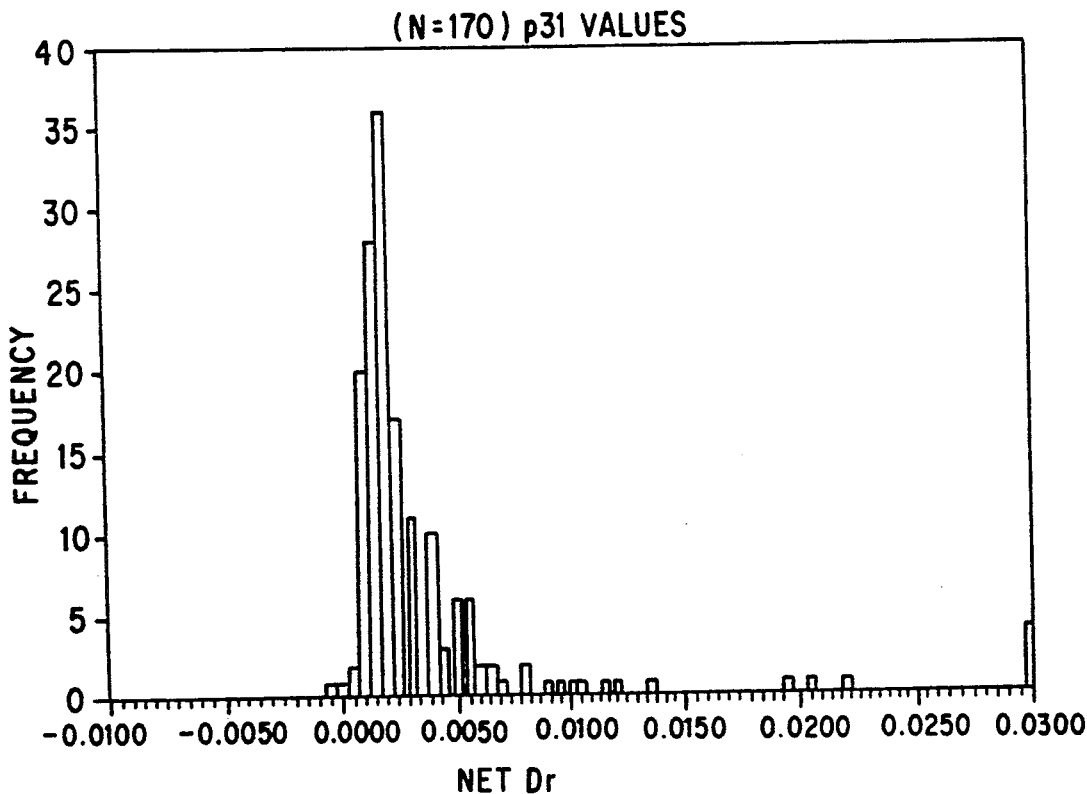
Figure 6:
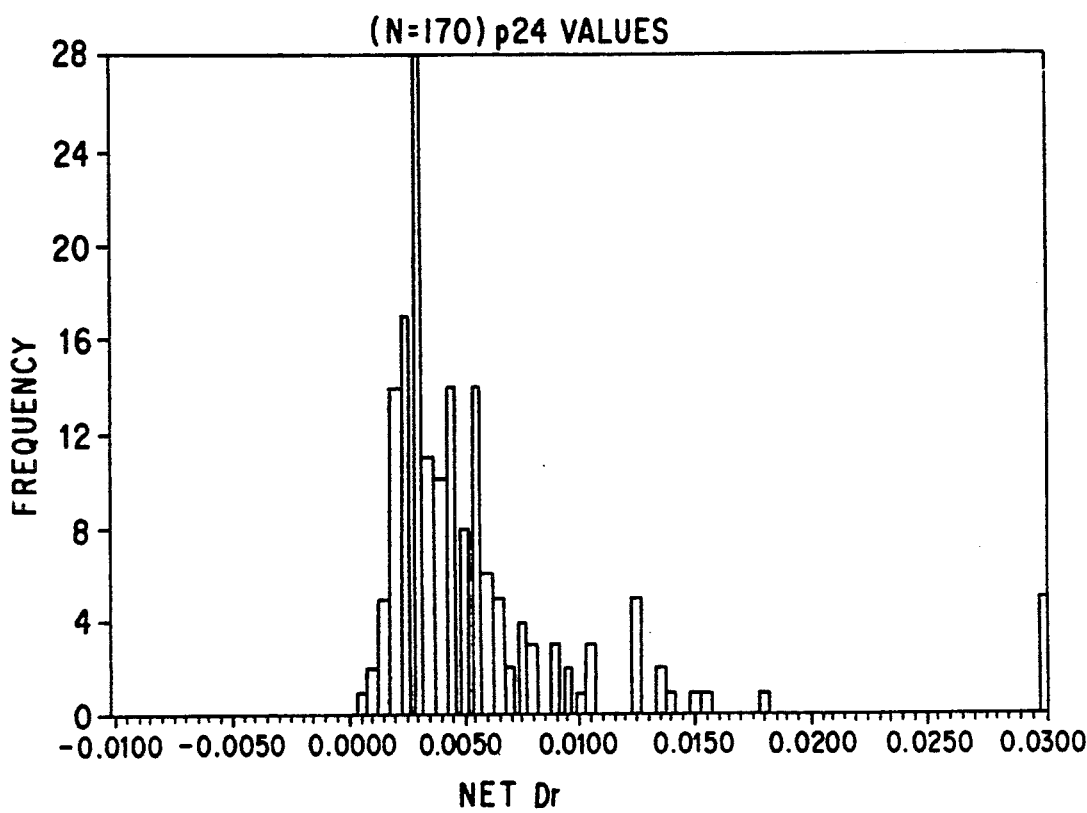
Figure 7:
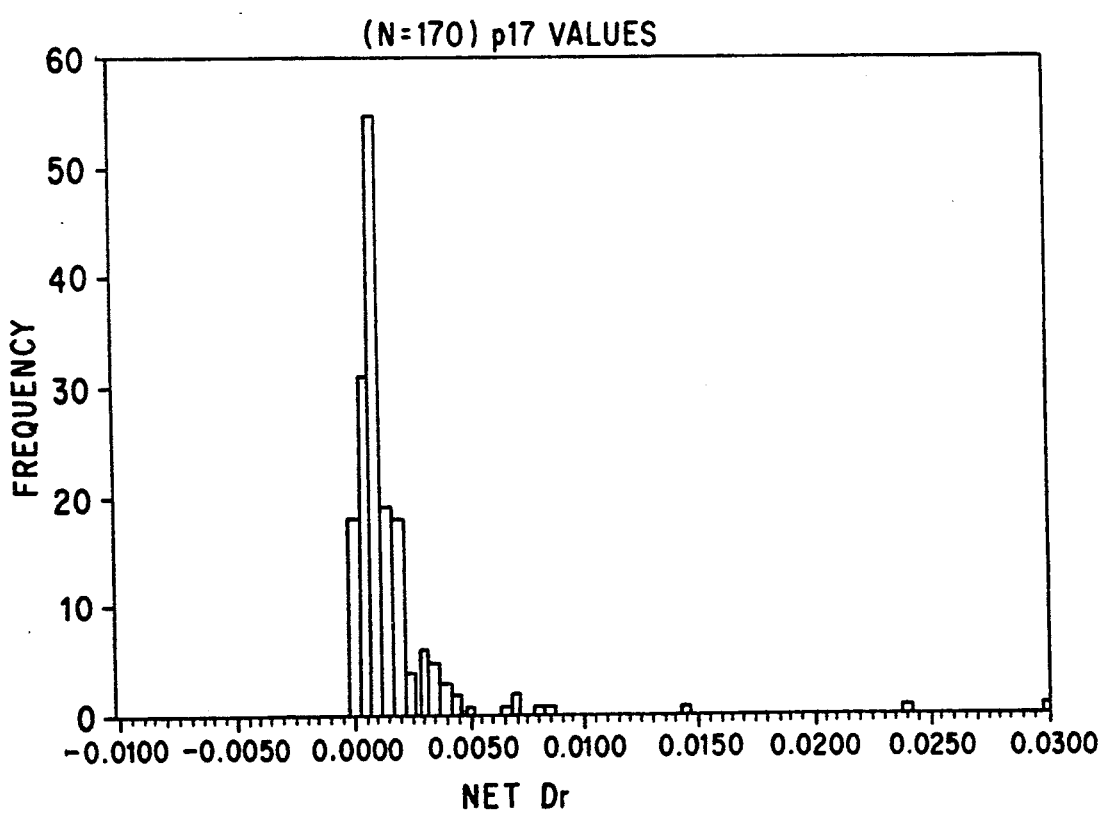
Figure 8:
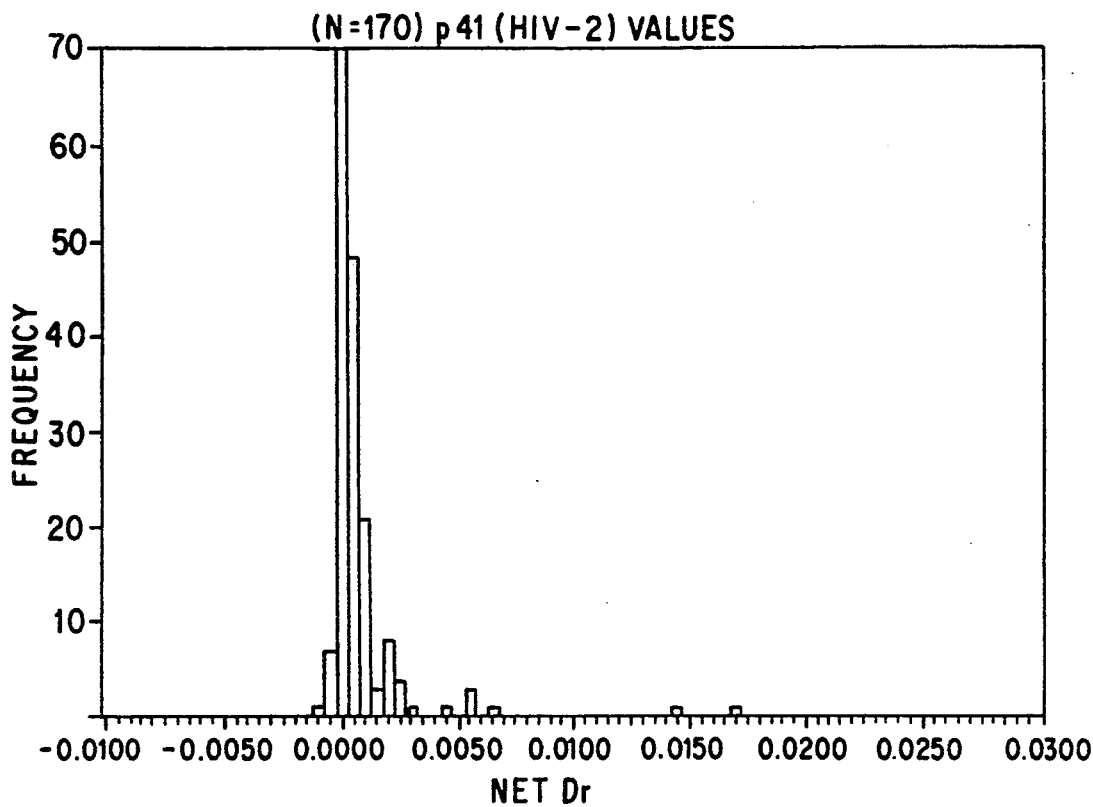
Figure 9:
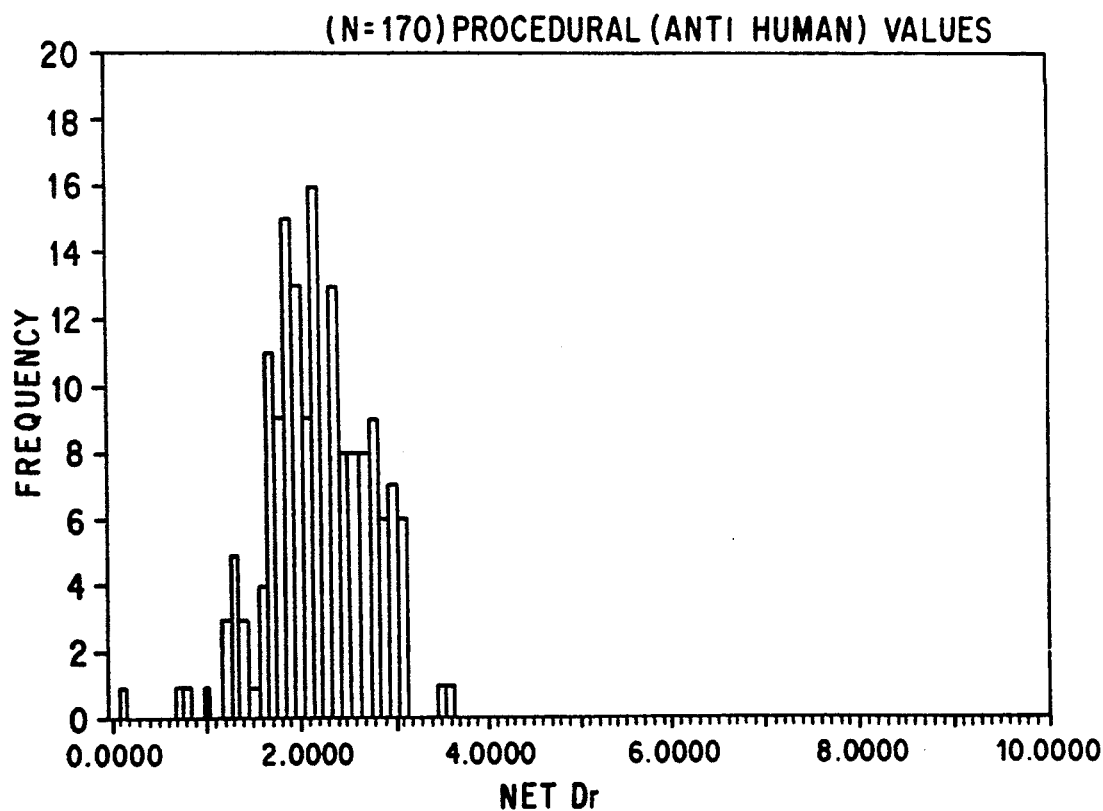

An assay system was designed to circumvent the problems of known screening and WB confirmatory tests. The present invention is a novel application of an immunoblot system suitable for the serodetection and confirmation of infections. Highly purified, diagnostically important antigens which are either from an infectious agent or recombinant DNA sources are immobilized individually on a solid support. We have discovered that greater sensitivity may be accomplished by using increased amounts of purified antigens. The amount of antigen immobilized on a solid support can vary from about 0.010 to about 5.0 ug. Preferably, the range will vary from about about 0.020 to about 2.0 ug. Most preferably, the range will vary from about 0.020 to about 1.0 ug.

In a preferred embodiment, the antigens are immobilized individually in an array of dots separated by moats on a sheet of nitrocellulose backed by inert plastic such as mylar. This arrangement is described as a test card in pending U.S. patent application Ser. No. 227,272, previously incorporated herein by reference. These antigen-dotted nitrocellulose cards are housed in individual reaction cartridges and then incubated at 22° to 37° C. with test sample for a time and under conditions sufficient to detect any specific antibodies which may be present in the test sample. These reaction cartridges are described in pending U.S. patent application Ser. No. 227,590 entitled "Reaction Cartridge and Carousel For Biological Sample Analyzer," previously incorporated herein by reference. Using a biotin-anti-biotin (BAB) amplifying immuno-detection system optimized for maximal sensitivity as the conjugated signal-generating system which yields a quantitatively measurable signal, specific antibodies present in the test sample to the various antigens immobilized on the solid support are simultaneously detected. These reaction cartridges containing the test cards are processed in an analyzer, thus rendering the incubations and washings semiautomated. The intensities of the color reactions are automatically quantitated by a reflectance reader which measures the density of reflectance (Dr) and the results are printed out in a digital format. Results are determined by comparing the Dr value(s) obtained from the test specimen to the Dr value(s) obtained from a normal negative population. Bar codes on the cartridges are used to assure positive sample identification. The analyzer used to process these test cards is an Abbott MATRIX TM analyzer, available from Abbott Laboratories, Abbott Park, Ill. The analyzer is the subject of pending U.S. patent application Ser. No. 227,408, previously incorporated herein by reference.

The semiautomated and optimized nature of the present assay system thus reduces hands-on time as well as assay time. Unlike the overnight incubation required for the WB test, the current invention requires only about 4 to 6 hours to produce results. Also, the current invention provides an automated digital print-out for the reactivity of each antigen on the solid support based on a reflectance density, thus eliminating subjectiveness when determining results.

A procedural control, for example, one that contains goat anti-human IgG, is included on the solid support to serve as an internal control to validate each test. A positive reaction on the solid support indicates that a test sample was added and that all reagents used in the subsequent incubation steps were added correctly and functioned properly. A positive procedural control is recommended for interpretation of the reactivities which occur on the solid support. It is also recommended that a reference spot coated with inert material, for example, casein acid hydrolysate, be included on the solid support.

The solid support may be any material with sufficient surface porosity to allow access by detection antibodies and a suitable surface affinity to bind antigens. Microporous structures are generally preferred, but materials with gel structure in the hydrated state may be used as well. Useful solid supports include:

natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers;

natural polymers containing nitrogen, such as proteins and derivatives, including cross-linked or modified gelatin;

natural hydrocarbon polymers, such as latex and rubber;

synthetic polymers which may be prepared with suitably porous structures, such as vinyl polymers, including polyethylene, polypropylene, polystyrene, polyvinylchloride, polyvinylacetate and its partially hydrolyzed derivatives, polyacrylates, polyacrylamides, polymethacrylates, copolymers and terpolymers of the above polycondensates, such as polyesters, polyamides, and other polymers, such as polyurethanes or polyepoxides;

porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as fillers with the above polymeric materials); and mixtures or copolymers of the above classes, such as graft copolymers obtained by initiating polymerization of synthetic polymers on a pre-existing natural polymer.

All these materials may be used in suitable shapes, such as films, sheets, or plates, or they may be coated onto or bonded or laminated to appropriate inert carriers, such as paper, glass, plastic films, or fabrics.

The porous structure of nitrocellulose has excellent absorption and adsorption qualities for a wide variety of reagents which may be used in connection with this invention and is a preferred support material. Nylon also possesses similar characteristics and is a suitable support material.

The solid support is preferably in the form of sheets of thickness from about 0.01 to 0.5 mm, preferably about 0.1 mm. The pore size may vary within wide limits, and is preferably from about 0.025 to 15 microns, especially from 0.15 to 15 microns.

The surfaces of these supports may be activated by chemical processes which cause covalent linkage of the antigen or immunoglobulin to the support. The irreversible binding of the antigen or antibody is obtained, however, in general, by adsorption on the porous material by poorly understood hydrophobic forces. A preferred support based on nitrocellulose is sold under the tradename Millipore ® by the firm Millipore, Bedford, Mass. Suitable supports also are described in U.S. patent application Ser. No. 227,272.

Figure 11:
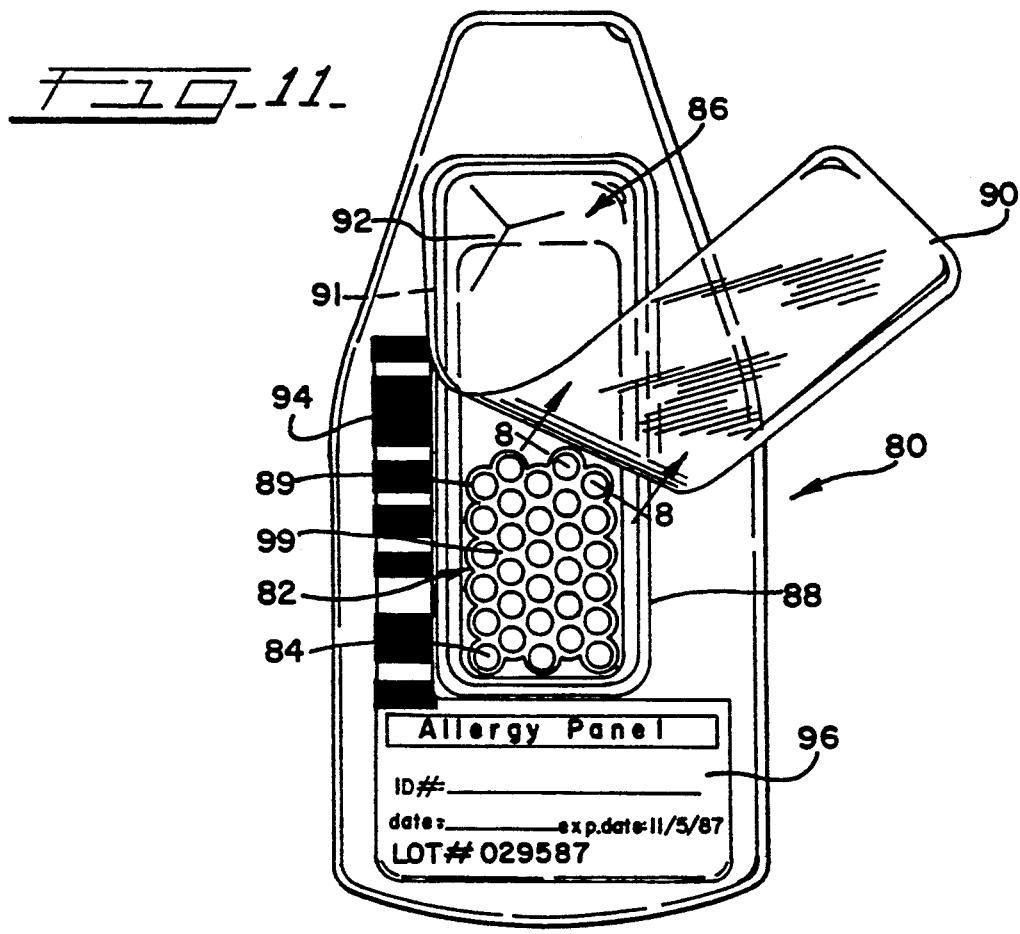
FIG. 11 is an enlarged top plan view of a preferred embodiment of a reaction cartridge support having a well containing a test card which has discrete test sites with moats.

A preferred support is test card 82, as illustrated in FIG. 11. Test card 82 preferably contains circular depressions 89 in the binding layer material which create an array of isolated test sites 84 preferably in close proximity to each other and each composed of binding layer material encircled by a moat 99 of air space. Test card 82 is preferably adhered to reaction cartridge 80 using two-sided adhesive tape on the bottom of reaction well 86, which is defined by well wall 88. Reaction well 86 is preferably provided with a removable, preferably transparent well cover 90 which preferably includes a reagent port 92 to facilitate the delivery and removal of fluids from the reaction well 86. The reaction cartridge 80 also preferably includes code means 94, such as an optical bar code, adapted to be read by an optical reader (not shown) and which is attached to or printed directly on the flat surface 91. The reaction cartridge 80 also preferably includes a panel 96 which may include information such as the expiration date of the particular reaction cartridge, the lot number of the particular panel of capture reagents or assay binding components and the like.

Figure 12:
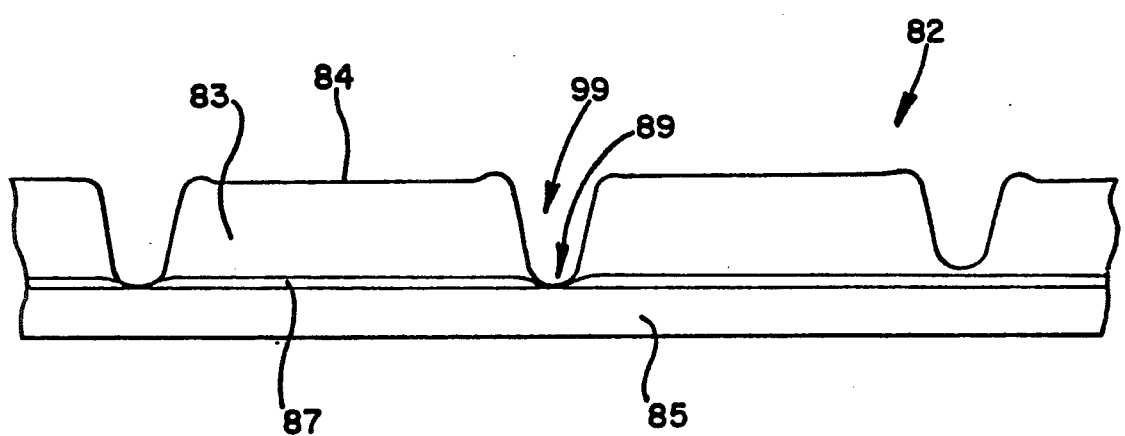
FIG. 12 is a magnified view, partially cutaway, through lines 8—8 (FIG. 11) showing sample test sites and moats in a preferred laminate structure of the test card.

FIG. 12 is a magnified view, partially cutaway, through lines 8—8 of FIG. 11 showing sample test sites and moats in a preferred laminate structure of the test card. The test card is preferably a laminate structure comprising a binding layer 83 adhered to a non-absorbent substrate 85 using an adhesive 87. The porous structure of nitrocellulose has been found to have excellent absorption and adsorption qualities for a wide variety of fluid capture reagents which may be used in connection with the invention and is therefore preferred for binding layer 83. Polyester film such as MYLAR plastic having a thickness of approximately 0.002 inches is suitable for non-absorbent substrate 85. An adhesive backed polyester film is commercially available from several sources, such as Flexcon (Spencer, MA).

A different antibody or antigen is delivered to each test site 84 so that a single sample can be simultaneously tested for the presence of binding components specific to each of a panel of different capture reagents. Some test sites 84 may have analyte delivered thereto to serve as positive control sites and some may have not reagent delivered thereto, to serve as negative control or reference sites. Preferably, from about 1.25 to 4 $\mu$L of antibody or antigen solution is delivered to each test site 84 using any number of suitable delivery methods including reagent jetting, metered air pulsing, positive displacement pump, or by capillary tube lowered to the surface of the test site 84.

After the test sites 84 of a test card 82 are spotted with antibody or antigen, the test sites are allowed to dry thoroughly at room temperature. After drying is complete, the binding layer 83 of test card 82 is preferably "blocked" with a protein coating such as inactivated horse serum or fish gelatin. Blocking masks potential non-specific binding sites on the binding layer 83. Suitable blocking is obtained during an incubation period of about 1 hour at approximately 37° C. and is preferably accomplished in tanks with agitation during incubation. Following blocking, the test card 82 is washed, such as with 10 mM Tris buffered saline, and allowed to dry overnight.

While the number of antigens or epitopes of antigens that may be analyzed is limited only by the size of the support, their variety and composition are limitless. Antigens having similar sizes but isolated from different sources are possible because they may be transferred from different gels to different discrete regions (sites) of the solid support. Reduction-sensitive or reduction-dependent antigens are conveniently handled by resolving them in separate preparative gels. In addition, the quantities of each antigen may be controlled and balanced to optimize assay selectivity and sensitivity.

Any desired number of antigens of one infectious agent, or combinations of antigens of several infectious agents, or any desired number of immunoglobulins of one infectious agent, or combinations of immunoglobulins of several infectious agents may be included on a single solid support and then analyzed in a single test procedure. This invention may be used to monitor concentrations of antibodies or detect antigens which are normally endemic, but which may vary in a pathological condition, or to detect and quantitate antibodies or antigens which only are found in a pathological condition. The present format also lends itself to use in combination assays which allow for the simultaneous detection of a panel of multiple antigens or antibodies, such as antigens or antibodies of HTLV-1, HBV, HCV, CMV, HSV, HPV, Human T Lymphotrophic Virus Type 1 (HTLV-1), Hepatitis B Virus (HBV), Hepatitis C Virus (HCV), Cytomegalovirus (CMV), Herpes Simplex Virus (HSV) and Human Papilloma Virus (HPV), etc., bacterial antigens or antibodies, fungal and other microbiological antigens and antibodies. Such combinations are ones of preference which can be determined by the routineer.

Test samples of bodily fluids such as serum, plasma, cerebrospinal fluid, urine, lymphatic fluid, milk, saliva, stools, and the like may be analyzed according to this invention.

It is contemplated that the detection of class-specific antibodies, such as IgG, IgA, IgE and IgM antibodies can be detected by choosing an appropriate second antibody, known to those of ordinary skill in the art. It further is contemplated that the system can be adapted to detect the presence of antigens by immobilizing specific antibodies, instead of antigens, on the solid support, with the appropriate change in the probing antibodies. Also, the choice of label used to produce the detectable signal can be determined by the routineer. Such contemplated labels include enzyme labels, luminescent labels such as fluorescent labels, chemiluminescent labels, and the like. It is contemplated that the detection-readout system can be changed depending upon the chosen label.

In an embodiment, the assay system for HIV was designed to test significant markers, and to exclude precursors such as gp160, p55, or regulatory proteins such as nef, VPR, and VPV. Thus, the HIV-1 markers gp120, p66, p41, p31, p24 and p17, and the HIV-2 marker p41 were tested in the assay system of the current invention without loss of sensitivity or specificity. In the particular case of HIV gp120, the antigen was non-reduced to preserve maximal reactivity. Compared to the WB test, the current invention yielded increased sensitivity, especially for HIV-1 gp120, p41, p31, and p66. A strongly reactive serum will yield a full pattern of reactivity to all HIV antigens, unlike the WB test which often gives an artifically biased and unproportionately strong p24 reactivity. In a preferred embodiment, the current invention also employs an amplifying biotin-anti-biotin:alkaline phosphatase signal generating system, which increases sensitivity by as much as 10-fold over that of the conventional immunoperoxidase procedures.

The specificity problems of traditional screening and WB tests with respect to HIV were reduced by utilizing recombinant antigens expressed in E. coli for HIV antigens except HIV-1 gp120. Gp120 was expressed in mammalian CHO cells and purified to >90% homogeneity as determined by SDS-PAGE analysis. The bacterial antigens were electrophoretically pure, monomeric antigens, which were essentially free from impurities, aggregates or degraded fragments.

The current invention provides for the simultaneous detection and differentiation of HIV-1 and HIV-2 antibodies by using recombinant HIV-1 p41 and HIV-2 p41 antigens that are capable of differentiating between these two viral types. This selection was based on the observation that the p41 antibodies are the most prevalent serological markers for both types of HIV infections and that there is minimal cross-reactivity between the two types of antibodies. Thus, this single test is capable of detecting both HIV-1 and HIV-2 antibodies, as well as differentiating between the two types.

The present invention will now be described by way of specific examples, which are meant to illustrate, but not to limit, the scope of the invention.

EXAMPLES

EXAMPLE 1

Preparation of HIV-1 and HIV-2 Test Cards

The HIV-1 recombinant antigens used were gp120, p66, p41, p31, p24 and p17. The HIV-2 antigen used was p41. All antigens were full length antigens with the exception of HIV-1 p41 and p66, and HIV-2 p41. The HIV-1 p41 antigen had a minor deletion of 38 amino acids in the transmembrane region, and the HIV-2 p41 antigen consisted of the immunodominant N-terminal one third of the transmembrane protein. All recombinant antigens were expressed in E. coli except the HIV-1 gp120 protein, which was expressed in mammalian CHO cells.

All recombinant antigens except gp120 were first partially purified. The partially purified proteins then were individually fractionated on 6 mm preparative SDS-PAGE gels. Protein bands were visualized by a cold KCl technique, modified from that of L. P. Nelles et al., Anal. Biochem. 73:522-531 (1976). The bands which contained the antigens of interest were excised from the gel. Such band-purified proteins then were recovered by electroelution and applied directly onto dots of nitrocellulose welded on sheets of mylar or other plastics. Gp120 was purified by chromatographic methods to >90% purity and then used directly for spotting.

The amount of each antigen applied per dot ranged from 0.01 to 1.0 ug, depending upon its reactivity against given dilutions of positive control sera. The antigens applied onto the array of dots by means of a multiple syringe-pump applicator were allowed to air dry at room temperature for at least twelve (12) hours. The sheets then were immersed with continuous gentle agitation in a blocking solution for approximately one (1) hour to saturate remaining blocking sites on the nitrocellulose surface. The blocking solution contained 1% gelatin, 1% casein acid hydrolysate, 5% Tween 20 in 20 mM Tris pH 7.5 and 500 mM NaCl, although other blocking solutions, known to those of ordinary skill in the art, can be used. The soproduced sheets were dried at 37° C. for approximately 30 minutes.

Individual 30 dot-arrays were punched out of the sheets and affixed to the bottom of plastic reaction cartridges. Clear self-sticking mylar lids then were fitted over the reaction cartridges. Each lid contained a 6 mm hole to permit pipetting and the introduction of a filler/aspirator probe. These assembled reaction cartridges then were stored at 2° to 8° C. until used. FIGS. 11 and 12 are drawings of the reaction cartridge (10) containing a test card (12), wherein discrete test sites (14) are separated by moats (16). FIG. 13 is a cross-section of the test card wherein discrete test sites (14) in nitrocellulose (18) are separated by moats (16), and the nitrocellulose (18) is backed by a layer of an inert plastic (mylar) (20).

EXAMPLE 2

Assay Procedure

Reaction cartridges prepared as described in Example 1 were placed on a circular tilt-spin platform in the Abbott MATRIX ™ instrument (available from Abbott Laboratories, Abbott Park, Ill.). One (1) ml of sample diluent, containing 15 mM Tris, 150 mM NaCl, 0.1% EDTA, 2.9% fish gelatin, 7.5% E. coli lysate, 0.02% goat immunoglobulin, 0.02% rabbit immunoglobulin, 0.5% non-fat dry milk, 0.5% Brij 35, 0.025% CKS protein and 1.0% bovine albumin, pH 7.4 to 7.6, was added to each reaction cartridge. Then, 10 to 100 ul of test sample was added to the cartridges, and the cartridges were incubated at 35° C. with continuous rotation for approximately one (1) hour. The incubated samples then were withdrawn by an automated filler-/aspirator and discarded into a waste container with disinfectant. A wash was performed by pumping one (1) ml of Tris buffered saline wash solution (TBS, containing 10 mM Tris, pH 7.4 and 150 mM NaCl) through the filler/aspirator and incubating the cartridges with rotation for several minutes. This wash cycle was repeated four times. Then, one (1) ml of an antibody solution of goat anti-human IgG (heavy and light chain):biotin conjugate diluted in buffer containing 15 mM Tris, 150 mM NaCl, 0.1% EDTA, 0.5% Brij 35, 0.5% non-fat dry milk, 0.02% goat immunoglobulin and sodium azide (0.1%) at pH 7.4 to 7.6, was added. The cartridges containing this mixture were incubated for approximately 1 hour at 35° C., and then this mixture was removed. The cartridges were washed three times as previously described. Next, one (1) ml of a second antibody solution consisting of rabbit anti-biotin:alkaline phosphatase conjugate diluted in a buffer containing 0.1M Tris, 154 mM NaCl, 0.02% $MgCl_2$, 0.0014% $ZnCl_2$, 1.0% normal rabbit serum, 5.0% fish gelatin, 0.1% polysorbate 20 and 0.1% sodium azide, pH 6.9 to 7.1, was added. After approximately one (1) hour of incubation at 35° C., the cartridges again were siphoned and washed three times as previously described. Next, one (1) ml of an alkaline phosphatase substrate solution consisting of 5-bromo-4-chloro-3-indoyl phosphate (BCIP) was added. A color reaction was allowed to develop for approximately 30 minutes at 35° C. with rotation. The cartridges again were washed three times. The lids were removed with a pair of forceps and the cards were allowed to dry for 15 to 30 minutes in the tilt-spin incubator. The cards then were sequentially scanned by a reflectance reader and the net reflectance densities were printed. The net density of reflectance value of the test sample was calculated by subtracting the background signal from the sample value.

EXAMPLE 3

Sensitivity of Serially Diluted Positive Samples

An HIV-1 positive sample was serially diluted two-fold from 1:32 to 1:4096 and the dilutions were tested by the Abbott MATRIX TM system as described by Examples 1 and 2, and by the Biotec TM WB assay system (available from DuPont, Wilmington, DE.). These results are reported in FIG. 1. Referring to FIG. 1, the assay system of the present invention detected the HIV-1 p41 antigen seven dilutions beyond the end-point titer of the WB test. Likewise, the HIV-1 gp120, p31, p66 and p24 antibody titers detectable by the present invention were one to four dilutions greater than the comparative corresponding titers obtained by the WB test. Thus, the data demonstrate that the assay system of the current invention was able to detect antibodies in more highly diluted test samples than those detected by the WB test.

EXAMPLE 4

Sensitivity of Seroconversion Panels

Ten (10) seroconversion panels comprising serial bleeds from ten (10) individuals taken during their seroconversion period from HIV-1 seronegativity to HIV-1 seropositivity, were tested by the assay system of the current invention and by the Biotec TM WB assay system (DuPont). The panels consisted of a total of 48 samples from the ten individuals. The data obtained from these panels are presented in Table 1. The data indicate that the assay system of the current invention detected all antibodies except HIV-1 p24 earlier than the WB test. In the case of p24, the two tests were equivalent. Also, it should be noted that the assay system of the current invention gave fairly strong positive reactions with some of the earlier bleed samples while the WB test yielded no reaction with these same samples. This was particularly demonstrated with HIV-1 p41, p66 and p31 antigens. The assay system of the present invention detected p41 antibodies several weeks earlier than the WB test. Further, it should be noted that of the 48 test samples, the present invention detected 37/48 seropositives while the WB test detected 18/48.

EXAMPLE 5

Screening of 170 Random Donors

The reactivities of 170 random donor samples were quantitated by Dr measurements obtained by following the methods of Examples 1 and 2. All 170 donors were seronegative. The results are shown in FIGS. 2 to 9. Referring to FIGS. 2 to 9, low Dr values for each antigen fell into a close cluster which were regarded as average background values for the antigen in question. However, a few samples gave slightly elevated values, which were below the visible level, i.e., Dr <0.03.

EXAMPLE 6

Testing of 91 Known Negative WB Indeterminates

In order to compare the specificities between the current invention and the WB test, 91 samples previously determined to be "indeterminates" by the WB test (DuPont) were retested in a side-by-side comparison of the WB test and the present invention. The data are presented in Table 2. Six (6) HIV-1 positive samples were included in the panel and tested positive by both assays. Of the remaining 91 samples, the present invention identified 71 as negative samples and 20 as "indeterminates". In contrast, 91 samples retested indeterminate by the WB test. It further was determined that the 20 indeterminate samples by the present invention displayed atypical reactivity patterns which showed mainly HIV p31-only, p24-only, p17-only and gp120-only reactivities. These indeterminate samples may have been infected with HIV; however, such atypical reactivities are most likely due to non-specific cross-reactivities to either the HIV antigens in question, or the blocking reagents used in preparing the solid phase, such as gelatin or casein acid hydrolysate. Further testing on subsequent bleeds is required to ascertain the infectivity status of these 20 samples. Generally, if there is no contrary clinical, virological, or polymerase chain reaction (PCR) evidence, and if there is no evidence of subsequent seroconversion within six (6) months, such atypical or indeterminate samples can be considered false positives.

EXAMPLE 7

Testing of 81 EIA-False Positives

Eighty-one (81) donor sera which tested repeat reactive by a screening EIA for HIV-1, but which had been tested by the WB test and found to be unconfirmed by WB, were tested in the assay system of the present invention according to the methods of Examples 1 and 2. Of these 81 sera, there were 70 negatives, three (3) positives, and eight (8) indeterminates by the present invention. The indeterminates displayed atypical patterns of HIV-1 p31-only (4 samples), p24-only (1 sample), gp120-only (1 sample) and generalized elevated staining (2 samples).

EXAMPLE 8

Detection of Both HIV-1 and HIV-2 Antibodies

A test was developed using HIV-1 and HIV-2 p41 antigen prepared as described in Example 1 to differentiate antibodies to HIV-1 from HIV-2. The test as developed was based on the relatively low cross-reactivity thus far observed in WB tests between the envelope transmembrane antigens of these two viral strains. We have observed that the reactivity of a given HIV positive serum to its homologous HIV p41 antigen is usually about one hundred times stronger than the reactivity of the given HIV positive serum to the heterologous antigen. Therefore, the p41 reactivity ratio appears to be capable of serving as an indicator of the infecting viral type. Thirty-four (34) HIV-1 positive sera gave strong positive reactions with the HIV-1 antigens tested, particularly HIV-1 p41. These test sera gave less than 1% of the signal with the p41 antigen of HIV-2. Five (5) known HIV-2 positive sera gave strong reactivity to HIV-2 p41 and less than 1% of the signal with HIV-1 p41. It was observed that some HIV-2 sera weakly cross-reacted with HIV-1 p31, p66, p24 and p17 antigens. This finding, however, is consistent with the reported sequence homology and antigenic cross-reactivities of the gag and pol gene products of the two virus types.

EXAMPLE 9

Detecting Specific HIV-1 and HIV-2 Antibodies In Same Sample

A mixing experiment was conducted in which an HIV-1 positive serum was combined with an HIV-2 positive serum. Each serum alone reacted with its respective p41 antigen. It was determined that the combined specimen reacted with both p41 antigens. Thus, the assay system of the present invention was able to detect both HIV-1 and HIV-2 present antibodies in one test sample.

EXAMPLE 10

Evaluation of a Coded Panel of HIV-1 and HIV-2 Positive Sera

A coded panel of 60 test sera including both positive and negative sera obtained from individuals in the United States and West Africa was analyzed according to the present invention in order to evaluate the ability of the present invention to detect and distinguish between various single and dual reactivities of HIV-1 and HIV-2. Twenty-three (23) HIV negative, 9 HIV-1 positive, 12 HIV-2 positive, and 16 HIV-1 and HIV-2 reactive sera were detected. These results were confirmed with a battery of tests including Western blot, radioimmunoprecipitation assay (RIPA), specific monoclonal antibodies and various bead EIAs.

EXAMPLE 11

Evidence for Possible Dual Infection

A West African serum which showed dual p41 reactivities was found by competition studies to contain both HIV-1 and HIV-2 p41-specific antibodies. The competition was performed by adding viral lysates in the initial incubation with the serum sample. In the presence of the HIV-1 viral lysate, the HIV-1 p41 reactivity was removed, whereas the HIV-2 p41 signal was unaffected. Likewise, the HIV-2 viral lysate specifically competed out only the HIV-2 p41 signal. A combination of the two viral lysates was required to compete out both signals.

EXAMPLE 12

Preparation of HCV Test Card

An HCV test card was developed which consisted of the clone c100-3 chimeric polypeptide expressed in yeast (Kuo et al., Science 244:362-364 [1989]) plus recombinant HCV polypeptides expressed in E. coli that included those derived from pHCV-23 (c100 fragment, lacking the first 107 N-terminal amino acids)pHCV-29 (33C), pHCV-34 and pHCV-35 (putative core), and pHCV-45 (NS4/NS5 junction). All proteins were expressed as CMP-KDO synthetase (CKS) fusion proteins, except pHCV-35, which was expressed in a lambda pL expression system. In addition, each card contained two controls consisting of goat anti-human IgG (heavy and light chain and human IgG, and a reference spot to detect background signal which proved useful in verifying the assay. The preparations of the recombinant polypeptides were individually optimized for spotting onto the solid support of nitrocellulose. The preferred buffers, pH conditions, and spotting concentrations are summarized in Table 3. However, it was found that successful applications of the polypeptides to nitrocellulose also were accomplished at different pH values, detergent compositions and salt concentrations. After spotting, the solid support was dried overnight at 37° C., then rinsed two times with Tris-buffered saline (TBS, containing 20 mM Tris buffer, 0.5M NaCl, 0.1% $NaN_3$ pH 7.4 to 7.6). The solid support then was overcoated with a solution of porcine gelatin (1%), casein acid hydrolysate (1%), and Tween-20 (5%) in TBS for 30 minutes at 35° C. The solid support was rinsed an additional two times in TBS, and then dried at 37° C. before assembly into a test cell cartridge.

EXAMPLE 13

HCV Assay Procedure 20 ul of test sample was mixed with 2 ml of a specimen diluent which consisted of bovine serum albumin (1% w/v), non-fat dry milk (0.5%, w/v), yeast extract (0.03%, w/v), and E. coli lysate containing CKS protein (5%, v/v) in 20 mM Tris-buffered saline (pH 7.4-7.6) which contained Brij-35 ® (1.5%, v/v), EDTA (0.1%, w/v) and $NaN_3$ (0.1%). One (1) ml of the diluted test sample was transferred to a test cell prepared as described in Example 13. The test cells were incubated with test samples for one (1) hour at 35° C. This incubation was followed by sequential incubations each of 20 to 35 minutes, with a biotin-conjugated goat anti-human IgG (heavy and light chain)-specific antibody (Kirkegaard-Perry Laboratories, Gaithersburg, MD), an alkaline phosphatase-conjugated rabbit anti-biotin antibody, and 5-bromo-4-chloro-3-indolyl phosphate to produce the colored product (detectable signal) at the reaction site.

EXAMPLE 14

Seroconversion Detection

Figure 10:
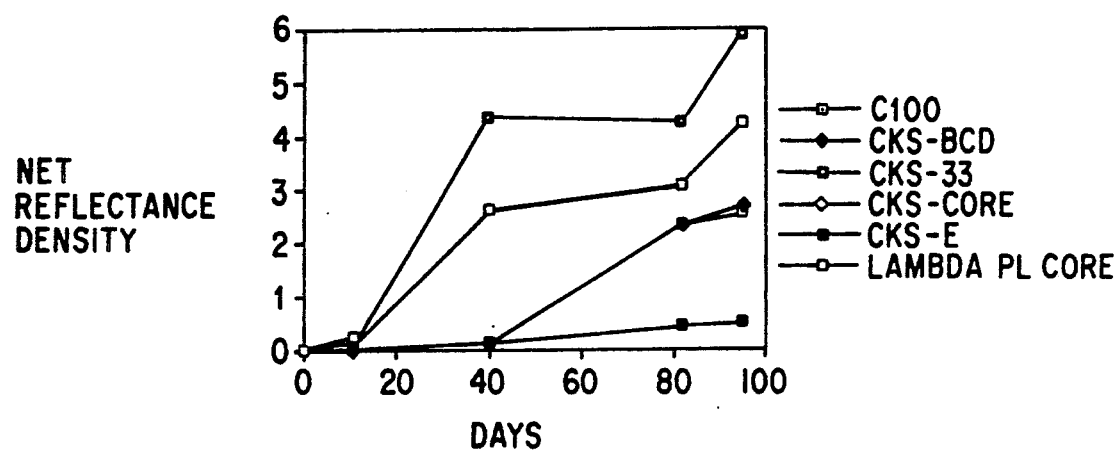
FIG. 10 is a graph of a seroconversion panel of specimen 02190-D to Hepatitis C Virus (HCV) using the assay system of the present invention which plots net reflectance density v. time (in days).

A seroconversion panel designated 02190-D was tested following Examples 12 and 13 for detectable reactivity of C100, CKS-BCD, CKS-33, CKS-CORE, CKS-E and Lambda pL core at 0, 15, 40, 80 and 95 days after exposure to HCV. As shown in FIG. 10, on day 11, each core protein signal increased between 15–18 fold over the days 0 signal. By day 40, recombinant proteins 33c and core were strongly reactive, whereas the c100 constructs and the NS4/NS5 junction protein were at or slightly below the cutoff value for reactivity.

EXAMPLE 15

Detection of Dilution Panel

Forty (40) normal donors were assayed by following the method of Example 13, using the test card of Example 12. The mean reflectance density value then was determined for each of the recombinant proteins. A cutoff value was calculated as the negative mean plus six standard deviations. Dilution panels of two samples also were tested. One sample (A00642) was from a convalescent non-A, non-B hepatitis patient, diluted in negative human plasma from 1:100 to 1:12800. The other sample (423) was from a paid plasma donor which tested positive in a HCV (c100) screening assay, diluted in negative human plasma from 1:40 to 1:2560. Sample to cutoff values (S/CO) were determined for all HCV recombinant proteins. Those S/CO values greater than or equal to 1.0 were considered reactive. The limiting dilution was defined as the lowest dilution at which the S/CO was greater than or equal to 1.0. As seen in Table 4, each sample tested positive for all HCV recombinant proteins. The data demonstrate that reactivity for sample A00642 was greatest with 33c antigen, and decreased for the remaining antigens c100, c100 fragment, NS4/NS5 junction protein and core, in the order listed. Sample 423 most strongly reacted with the recombinant proteins expressing 33c and the core regions, and to a lesser extent with the c100 fragment, NS4/NS5 junction protein and c100.

TABLE 1

| Panel | Draw Date | Western Blot | REFLECTANCE DENSITY (DR) VALUE ||||||| 
|---|---|---|---|---|---|---|---|---|---|
| | | | HIV-1 |||| HIV-2 |||
| | | | 120 | 66 | 41 | 31 | 24 | 17 | 41 |
| 6977 | 8-12 | 24 | — | 1.06 | 78.57 | — | 2.85 | — | — |
| | 8-17 | 24 | — | + | + | — | + | — | — |
| | 8-21 | 160, 41, 24 | 1.02 | + | + | 1.47 | + | — | — |
| | 8-27 | 160, 120, 41, 24 | + | + | + | + | + | — | — |
| | 8-31 | 160, 120, 41, 24 | + | + | + | + | + | — | — |
| 46402 | 12-14 | 24 | — | 1.57 | 65.77 | — | 1.44 | — | — |
| | 12-21 | 160, 24 | — | + | + | — | + | — | — |
| | 12-23 | 160, 24 | — | + | + | 2.13 | + | — | — |
| | 12-30 | 160, 66, 51, 24 | 2.18 | + | + | + | + | — | — |
| | 01-4 | 160, 66, 51, 24 | + | + | + | + | + | — | — |
| 46320 | | | 2.6 | 26.40 | 397.15 | 3.14 | 67.11 | — | — |
| | | | + | + | + | + | + | — | — |
| 3988 | 3-9 | — | — | — | — | — | — | — | — |
| | 3-11 | — | — | — | — | — | — | — | — |
| | 3-16 | 24 | — | — | 0.91 | — | — | — | — |
| | 3-18 | 24 | — | — | 13.07 | — | 1.09 | — | — |
| | 3-25 | 160, 41, 24 | — | 1.06 | + | — | + | — | — |
| | 3-28 | 160, 41, 24 | 1.24 | + | + | 1.66 | + | — | — |
| 6108 | 11-16 | 24 | 2.24 | 1.2 | 114.81 | — | 2.73 | — | — |
| | 11-20 | 55, 24 | + | + | + | — | + | — | — |
| | 11-24 | 55, 24, 17 | + | + | + | — | + | 1.19 | — |
| | 11-27 | 55, 41, 24, 17 | + | + | + | — | + | + | — |
| | 12-1 | 160, 120, 55, 41, 24, 17 | + | + | + | — | + | + | — |
| | 12-4 | 160, 120, 66, 55, 41, 24, 17 | + | + | + | — | + | + | — |
| | 12-8 | 160, 120, 66, 55, 51, 41, 24, 17 | + | + | + | 1.43 | + | + | — |
| | 12-11 | 160, 120, 66, 55, 51, 41, 24, 17 | + | + | + | + | + | + | — |
| 72593 | 12-15 | 24 | 1.00 | 1.53 | 66.65 | — | 2.84 | — | — |
| | 12-17 | 24 | + | + | + | — | + | — | — |
| | 12-24 | 160, 120, 24 | + | + | + | 1.03 | + | — | — |
| | 12-30 | 160, 120, 24 | + | + | + | + | + | 0.93 | |
| | 01-5 | 160, 120, 24 | + | + | + | + | + | 1.48 | |
| | 01-7 | 160, 120, 24 | + | + | + | + | + | + | |
| 1066 | | | — | — | — | — | — | — | — |
| | | | — | — | — | — | — | — | — |
| | | | — | — | 37.92 | 1.22 | 108.54 | — | — |
| | | | — | 0.94 | + | + | + | — | — |
| | | | 1.01 | 6.59 | + | + | + | — | — |
| | | | + | + | + | + | + | — | — |
| | | | + | + | + | + | + | — | — |
| G | 1 | — | — | — | — | — | — | — | — |
| | 2 | — | — | — | — | — | — | — | — |
| | 3 | — | — | — | — | — | — | — | — |
| | 4 | — | — | — | 24.76 | — | — | — | — |
| | 6 | 24 | — | — | + | — | — | — | — |
| | 7 | 24 | — | — | + | — | 1.35 | — | — |
| | 8 | 41, 24 | — | 2.04 | + | — | + | — | — |
| | 9 | 41, 24 | — | + | + | 1.04 | + | — | — |
| | 10 | 41, 24 | 1.13 | + | + | + | + | — | — |
| | 11 | 41, 24 | + | + | + | + | + | 6.48 | — |
| | 12 | 120, 41, 24 | + | + | + | + | + | + | — |

TABLE 1-continued

| Panel | Draw Date | Western Blot | REFLECTANCE DENSITY (DR) VALUE | | | | | | |
|---|---|---|---|---|---|---|---|---|---|
| | | | HIV-1 | | | | HIV-2 | | |
| | | | 120 | 66 | 41 | 31 | 24 | 17 | 41 |
| 13078 | 4-23 | — | — | — | — | — | — | — | — |
| | 4-28 | — | — | — | 1.37 | — | — | — | — |
| | 4-30 | — | — | — | + | — | — | — | — |
| | 5-5 | 24 | — | — | + | — | 1.18 | — | — |
| | 5-8 | 24, 41, 55 | — | — | + | — | + | — | — |
| | 5-12 | 24, 41, 55 | — | — | + | — | + | — | — |
| | 5-17 | 24, 41, 55 | — | — | + | — | + | — | — |
| 103524 | 10-20 | 66, 41, 24 | — | 1.16 | 36.63 | — | 15.23 | — | — |
| | 10-24 | 66, 55, 41, 24 | — | + | + | — | + | — | — |
| | 10-27 | 66, 55, 51, 41, 24 | 2.22 | + | + | 1.33 | + | — | — |

TABLE 2

HIV-1 INDETERMINATE SPECIMENS BY WESTERN BLOT
Total Samples Tested = 97

| | Positive | Negative | Indeterminate |
|---|---|---|---|
| Western Blot | 6 | 0 | 91 |
| Present Invention | 6 | 71 | 20 |

TABLE 3

HIV-1 POLYPEPTIDE SPOTTING CONDITIONS

| PLASMID/PROTEIN | ng/SPOT | SPOTTING BUFFER |
|---|---|---|
| c100 | 100–150 | 20 mM Tris-HCl, 0.9% NaCl, 0.015% SDS, pH 8.3 |
| pHCV-23/CKS-BCD | 100–150 | 20 mM Tris-HCl, 0.9% NaCl, 0.015% SDS, pH 8.3 |
| pHCV-29/CKS-33c | 100–150 | 50 mM Naphosphate, 0.01% Triton X100, pH 6.5 |
| pHCV-35/CORE | 100–150 | 50 mM Tris-HCl, 0.0025% Tween 20, pH 8.5 |
| pHCV-34/CKS-CORE | 75–100 | 50 mM Naphosphate, 0.0025% Tween 20, pH 12.0 |
| pHCV-45/CKS-E | 100–150 | 50 mM Tris-HCl, 0.015% SDS, pH 8.5 |

TABLE 4

| ANTIGEN | REFLECTANCE DENSITY VALUES NEGATIVE | | LIMITING DILUTION | |
|---|---|---|---|---|
| | MEAN | CUTOFF | A00642 | 423 |
| c100-3 | 0.023 | 0.129 | 1600 | 40 |
| c100 Fragment | 0.011 | 0.050 | 3200 | 320 |
| c33c | 0.005 | 0.031 | 12800 | 2560 |
| CORE | 0.027 | 0.166 | 400 | 320 |
| | 0.038 | 0.180 | 400 | 1280 |
| NS4/NS5 Junction | 0.017 | 0.079 | 800 | 320 |

What is claimed is:

1. An immunoassay to simultaneously detect the presence or amount of more than one antibody which may be present in a test sample, said assay comprising:
   a. contacting a test sample of a species with a porous solid support backed by inert plastic on which said porous solid support more than one antigen is immobilized each on its own discrete test site which is isolated by a surrounding moat created by a depression which extends substantially through the porous solid support and which said porous solid support was treated with a blocking reagent after said antigens were immobilized, for a time and under conditions sufficient to form antigen-antibody complexes;
   b. contacting said antigen-antibody complexes with a conjugated signal generating system comprising an anti-species antibody which anti-species antibody binds to the antigen-antibody complexes and which antibody is conjugated to a detectable label which is capable of yielding a quantitatively measurable signal correlated to the signal of a normal negative test sample to indicate antibody positive or antibody negative for the test sample; and
   c. detecting the presence of said antigen-antibody complexes on said porous solid support by measuring the generated signal.

2. The immunoassay of claim 1 wherein the porous solid support is nitrocellulose.

3. The immunoassay of claim 1 wherein the discrete test site is an immunodot blot.

4. The immunoassay of claim 1 wherein the antibody detected is selected from the group consisting of anti-HIV-1 antibody, anti-HIV-2 antibody and anti-HCV antibody.

5. The immunoassay of claim 1 wherein the antibody detected is anti-HIV-1 antibody.

6. The immunoassay of claim 1 wherein the antibody detected is anti-HIV-2 antibody.

7. The immunoassay of claim 1 wherein the antibody detected is anti-HCV antibody.

8. The immunoassay of claim 1 wherein the solid support is contacted with a blocking reagent prior to contacting the solid support with the test sample.

9. The immunoassay of claim 1 wherein said label is selected from the group consisting of an enzyme, a luminescent label and a chemiluminescent label.

10. The immunoassay of claim 1 wherein said signal generating system is a biotin-anti-biotin amplifying system.

11. An immunoassay to simultaneously detect the presence or amount of more than one antigen which may be present in a test sample, said assay comprising:
   a. contacting a test sample with a porous solid support backed by inert plastic on which said porous solid support more than one antibody is immobilized each on its own discrete test site which is isolated by a surrounding moat created by a depression which extends substantially through the porous solid support and which said porous solid support was treated with a blocking reagent after said antigens were immobilized, for a time and under conditions sufficient to form antigen-antibody complexes;

b. contacting said antigen-antibody complexes with a conjugated signal generating system comprising at least one anti-antigen antibody which antibody binds to the antigen-antibody complexes and which antibody is conjugated to a detectable label which is capable of yielding a quantitatively measurable signal correlated to the signal of a normal negative test sample to indicate antigen positive or antigen negative for the test sample; and c. detecting the presence of said antigen-antibody complexes on said porous solid support by measuring the generated signal.

12. The immunoassay of claim 11 wherein the porous solid support is nitrocellulose.

13. The immunoassay of claim 11 wherein the discrete test site is an immunodot blot.

14. The immunoassay of claim 11 wherein the antigen detected is selected from the group consisting of HIV-1, HIV-2 and HCV.

15. The immunoassay of claim 11 wherein the antigen detected is HIV-1.

16. The immunoassay of claim 11 wherein the antigen detected is HIV-2.

17. The immunoassay of claim 11 wherein the antigen detected is HCV.

18. The immunoassay of claim 11 wherein the solid support is contacted with a blocking reagent prior to contacting the solid support with the test sample.

19. The immunoassay of claim 11 wherein said label is selected from the group consisting of an enzyme, a luminescent label and a chemiluminescent label.

20. The immunoassay of claim 11 wherein said signal generating system is a biotin-anti-biotin amplifying system.

* * * * *